United States Patent
Chen et al.

(10) Patent No.: US 12,397,091 B2
(45) Date of Patent: Aug. 26, 2025

(54) MILK BOWL AND WEARABLE BREAST PUMP

(71) Applicant: GUANGDONG HORIGEN MOTHER & BABY PRODUCTS CO., LTD., Shantou (CN)

(72) Inventors: Jianbiao Chen, Shantou (CN); Yongyou Lin, Shantou (CN); Changxin Chen, Shantou (CN); Yebin Cai, Shantou (CN)

(73) Assignee: GUANGDONG HORIGEN MOTHER & BABY PRODUCTS CO., LTD., Shantou (CN)

( * ) Notice: Subject to any disclaimer, the term of this patent is extended or adjusted under 35 U.S.C. 154(b) by 0 days.

(21) Appl. No.: 18/815,035

(22) Filed: Aug. 26, 2024

(65) Prior Publication Data
US 2025/0127966 A1   Apr. 24, 2025

Related U.S. Application Data

(63) Continuation-in-part of application No. PCT/CN2023/138353, filed on Dec. 13, 2023.

(51) Int. Cl.
*A61M 1/06* (2006.01)

(52) U.S. Cl.
CPC ............ *A61M 1/064* (2014.02); *A61M 1/067* (2021.05)

(58) Field of Classification Search
CPC ........ A61M 1/06; A61M 1/062; A61M 1/064; A61M 1/066; A61M 1/067
See application file for complete search history.

(56) References Cited

U.S. PATENT DOCUMENTS

| | | | | |
|---|---|---|---|---|
| 5,673,806 | A  * | 10/1997 | Busnel | A61J 11/0065 215/11.1 |
| 8,052,634 | B2 * | 11/2011 | Thommen | A61M 1/064 604/74 |
| 8,646,632 | B2 * | 2/2014 | Vischer | A61J 17/10 215/11.1 |
| 11,541,156 | B2 * | 1/2023 | Hwang | A61M 1/067 |
| 2006/0264816 | A1 * | 11/2006 | Silver | A61M 1/066 604/74 |
| 2014/0190357 | A1 * | 7/2014 | Mak | A47J 36/2438 99/453 |
| 2018/0028733 | A1 * | 2/2018 | Rigert | A61M 1/064 |

(Continued)

FOREIGN PATENT DOCUMENTS

| | | | | |
|---|---|---|---|---|
| KR | 10-1020581 | * | 3/2011 | ............ A61M 1/06 |
| WO | WO-2015021573 A1 | * | 2/2015 | ............ A61M 1/064 |
| WO | WO-2018017815 A1 | * | 1/2018 | .......... A61J 11/0065 |

*Primary Examiner* — Quynh-Nhu H. Vu

(74) *Attorney, Agent, or Firm* — Ming Jiang; OPENPTO US LLC

(57) ABSTRACT

Provided are a milk bowl and a wearable breast pump. The milk bowl is applied to the wearable breast pump, and includes a bowl body and an airbag. The bowl body is provided with a channel, a milk sucking port, a negative pressure port, a milk outlet and an airbag mounting groove. The milk sucking port, the negative pressure port and the milk outlet are spaced apart, and are all communicated with the channel. The negative pressure port is further communicated with the airbag mounting groove. The airbag is mounted in the airbag mounting groove. When the airbag in a natural state, the bottom of the airbag is in a wave shape.

17 Claims, 7 Drawing Sheets

(56) References Cited

U.S. PATENT DOCUMENTS

| | | | |
|---|---|---|---|
| 2019/0240386 A1* | 8/2019 | Larsson | A61M 1/75 |
| 2021/0369927 A1* | 12/2021 | Hwang | A61M 1/06 |
| 2023/0173149 A1* | 6/2023 | Fang | A61M 1/06 |
| | | | 604/74 |
| 2023/0211054 A1* | 7/2023 | Mou | A61M 1/06935 |
| | | | 604/74 |
| 2023/0364310 A1* | 11/2023 | Luo | A61M 1/064 |
| 2024/0001008 A1* | 1/2024 | Chen | A61M 1/064 |
| 2024/0001010 A1* | 1/2024 | Chen | A61M 1/066 |
| 2024/0216226 A1* | 7/2024 | Palladino | A61J 11/04 |

* cited by examiner

MILK BOWL AND WEARABLE BREAST PUMP

CROSS-REFERENCE OF RELATED APPLICATION

This application is a continuation-in-part of PCT application PCT/CN2023/138353 filed on Dec. 13, 2023, which claims priority to Chinese Patent Application No. 202322836993.3, filed on Oct. 23, 2023. All of these applications are herein incorporated by reference in their entireties for all purposes.

TECHNICAL FIELD

The present disclosure relates to the technical field of breast pumps, and particularly to a milk bowl and a wearable breast pump.

BACKGROUND

With the development of science and technology, wearable breast pumps are popular among lactating women, especially working women. The wearable breast pump can be worn directly on the user's body or integrated into the user's clothing or accessories, so as to release the breast milk that has accumulated in the breast, thus facilitating collection of the breast milk.

Generally, the wearable breast pump is provided with an airbag, a negative pressure environment in the breast pump is produced through inflation and deflation of the airbag, and negative pressure suction is thereby generated to suck the breast milk. However, in the related art, the wearable breast pump has insufficient negative pressure suction due to insufficient suction of the airbag, resulting in the inability of the wearable breast pump to suck the breast milk.

SUMMARY

The present disclosure provides a milk bowl and a wearable breast pump to alleviate at least one of the above technical problems.

For this, the embodiments of the present disclosure provide the following technical solutions:

In a first aspect, an embodiment of the present disclosure provides a milk bowl for a wearable breast pump. The milk bowl includes a bowl body and an airbag. The bowl body is provided with a channel, a milk sucking port, a negative pressure port, a milk outlet and an airbag mounting groove. The milk sucking port, the negative pressure port and the milk outlet are spaced apart, and are all communicated with the channel. The negative pressure port is also communicated with the airbag mounting groove. The airbag is mounted in the airbag mounting groove. When the airbag in a natural state, a bottom of the airbag is in a wave shape.

In a second aspect, an embodiment of the present disclosure provides a wearable breast pump. The wearable breast pump includes a main unit and a milk bowl. The main unit is assembled to the milk bowl. The milk bowl includes a bowl body, an airbag and a breast pump flange. The bowl body is provided with a channel, a milk sucking port, a negative pressure port, a milk outlet and an airbag mounting groove. The milk sucking port, the negative pressure port and the milk outlet are spaced apart, and are all communicated with the channel. The milk sucking port is communicated with the breast pump flange. The airbag mounting groove is communicated with the negative pressure port. The airbag is mounted in the airbag mounting groove. When the airbag in a natural state, a bottom of the airbag is in a wave shape.

BRIEF DESCRIPTION OF DRAWINGS

In order to more clearly illustrate the technical solutions in the embodiments of the present disclosure, drawings needed to be used in the description of the embodiments are briefly described below. Apparently, the drawings below are just some embodiments of the present disclosure, and other drawings can also be obtained by those skilled in the art based on these drawings without paying any creative effort.

DETAILED DESCRIPTION OF EMBODIMENTS

In order to enable those skilled in the art to better understand the embodiments of the present disclosure, the technical solutions in the embodiments of the present disclosure will be clearly and comprehensively described below in conjunction with drawings in the embodiments of the present disclosure. Apparently, the described embodiments are only a part rather than all of the embodiments of the present disclosure. All other embodiments, obtained by those skilled in the art based on the embodiments in the present disclosure without making any creative labor, shall fall within the scope of protection of the present disclosure.

Figure 1:
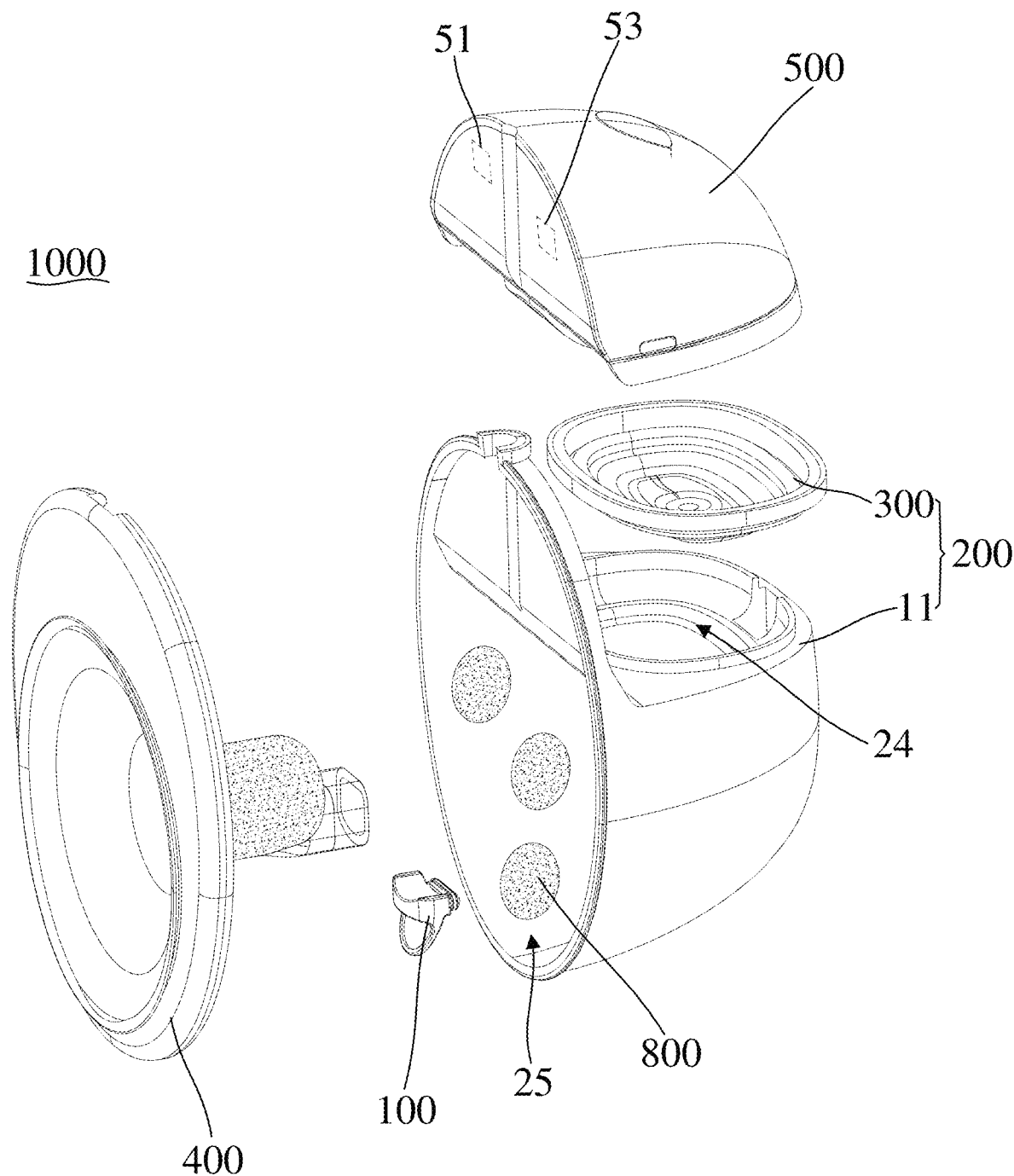
FIG. 1 is a schematic diagram illustrating a structure of a wearable breast pump provided by the embodiments of the present disclosure.
Figure 2:
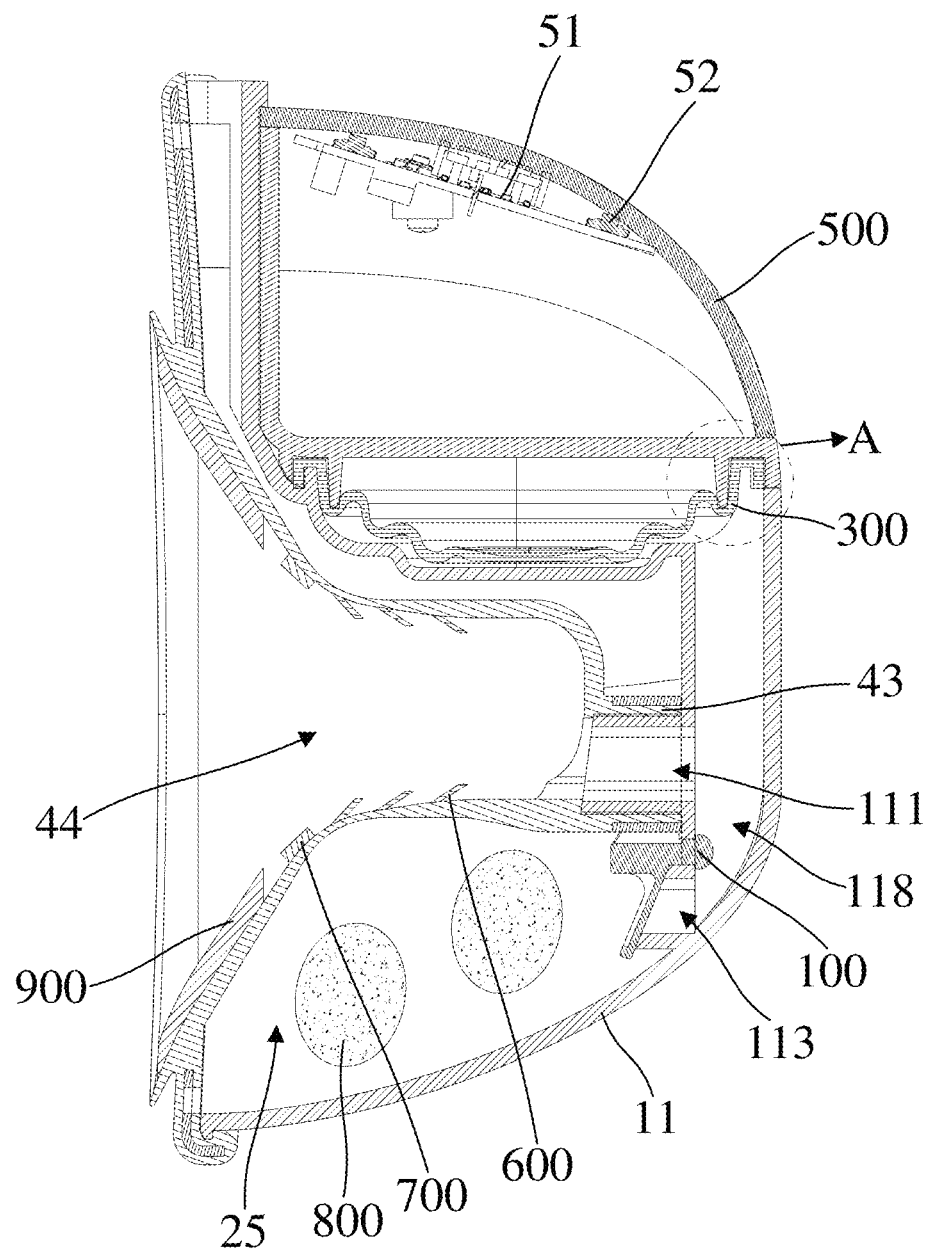
FIG. 2 is a longitudinal sectional view of the wearable breast pump of FIG. 1.

Referring to FIG. 1 and FIG. 2, the embodiments of the present disclosure provides a wearable breast pump 1000. The wearable breast pump 1000 can be worn on user's breast without holding the breast pump with the user's hand, which is convenient for the user to use.

In some embodiments, the wearable breast pump 1000 includes a main unit 500 and a milk bowl 200. The main unit 500 is assembled to the milk bowl 200. The milk bowl 200 includes a bowl body 11, an airbag 300 and a breast pump flange 400. The bowl body 11 is provided with a channel 118, a milk sucking port 111, a negative pressure port 112, a milk outlet 113 and an airbag mounting groove 24. The milk sucking port 111, the negative pressure port 112 and the milk outlet 113 are spaced apart, and are all communicated with the channel 118.

In this way, the bowl body 11 can meet the needs of the wearable breast pump 1000 for suction, inhalation and discharge, which helps to ensure the normal operation of the wearable breast pump 1000. The bowl body 11 integrates therein the channel 118, the milk sucking port 111, the negative pressure port 112 and the milk outlet 113, and there is no need to separately provide a three-way connector for the milk bowl 200. This facilitates reduction of the number of components of the milk bowl 200 and thus facilitates manufacture of the milk bowl 200; in addition, this also facilitates reduction of the number of molds of the members, and thus facilitates reduction of the mold cost of the milk bowl 200. Furthermore, the use convenience of the milk bowl 200 is also improved.

Figure 3:
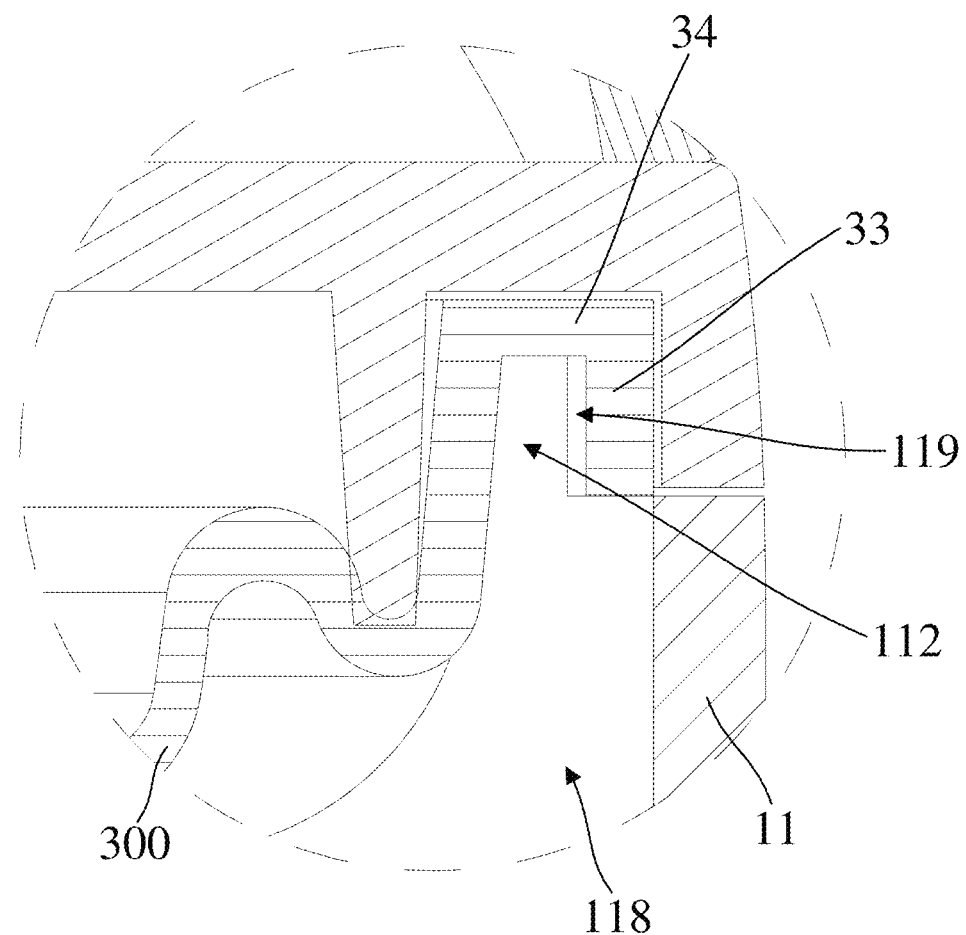
FIG. 3 is an enlarged view of part A in the wearable breast pump of FIG. 2.

Referring to FIG. 1 to FIG. 3, in some embodiments, the airbag mounting groove 24 is communicated with the negative pressure port 112, and the airbag 300 is mounted in the airbag mounting groove 24. The airbag 300 may be in a cuboid shape. The airbag 300 may be inflated for expanding or deflated for contraction, so that the negative pressure environment in the channel 118 is adjusted through the negative pressure port 112, thereby obtaining a suitable negative pressure environment in the channel 118. This ensures suitable negative pressure suction at the milk sucking port 111, to enable the breast milk to flow into the milk sucking port 111.

In some embodiments, when the airbag 300 in a natural state, the bottom of the airbag 300 is in a wave shape.

In this way, it is helpful to increase the initial area of the airbag 300, and the airbag 300 has high degree of deformation when the airbag 300 is contracted and expanded. For example, when the airbag 300 is inflated, it may be expanded in a wide margin to increase its own volume, so that the airbag 300 may also have a large volume change when being expanded. For another example, when the airbag 300 is deflated for contraction, it can reduce its own volume in a wide margin to increase the suction. This helpful to ensure sufficient suction of the airbag 300 to adjust the negative pressure environment in the channel 118, and also helpful to increase the adjustment range of the suction of the airbag 300, thereby better adjusting the negative pressure suction at the milk sucking port 111 to adapt to the user's use demand.

The natural state of the airbag 300 may mean a state in which the air pressure in the airbag 300 is equal or substantially equal to the air pressure in the external environment, or a state in which no gas is filled in the airbag 300 or the gas in the airbag 300 is not full. The airbag 300 may also be in an inflated state, and the airbag 300 in the inflated state is greatly expanded, so that the area of the airbag 300 in the inflated state is greater than the area of the airbag 300 in the natural state. The airbag 300 may also be in a negative pressure state, and the airbag 300 in the negative pressure state is greatly contracted, so that the area of the airbag 300 in the negative pressure state is smaller than the area of the airbag 300 in the natural state.

In some embodiments, the main unit 500 may include a power supply 51, a controller 52 and a vacuum pump 53. The controller 52 is electrically connected with the power supply 51. The controller 52 communicates with the vacuum pump 53 through signal, and the vacuum pump 53 is connected with the airbag 300.

In this way, the controller 52 may control the vacuum pump 53 to work without manual manipulation, which facilitates the use of the wearable breast pump 1000 by the user.

When the breast milk needs to be pumped, the breast pump flange 400 is placed on the breast, the controller 52 controls the vacuum pump 53 to work to pump the airbag 300 to a vacuum state, and a negative pressure is thus generated in the channel 118, which in turn generates negative pressure suction at the milk sucking port 111 to suck the breast milk.

Figure 4:
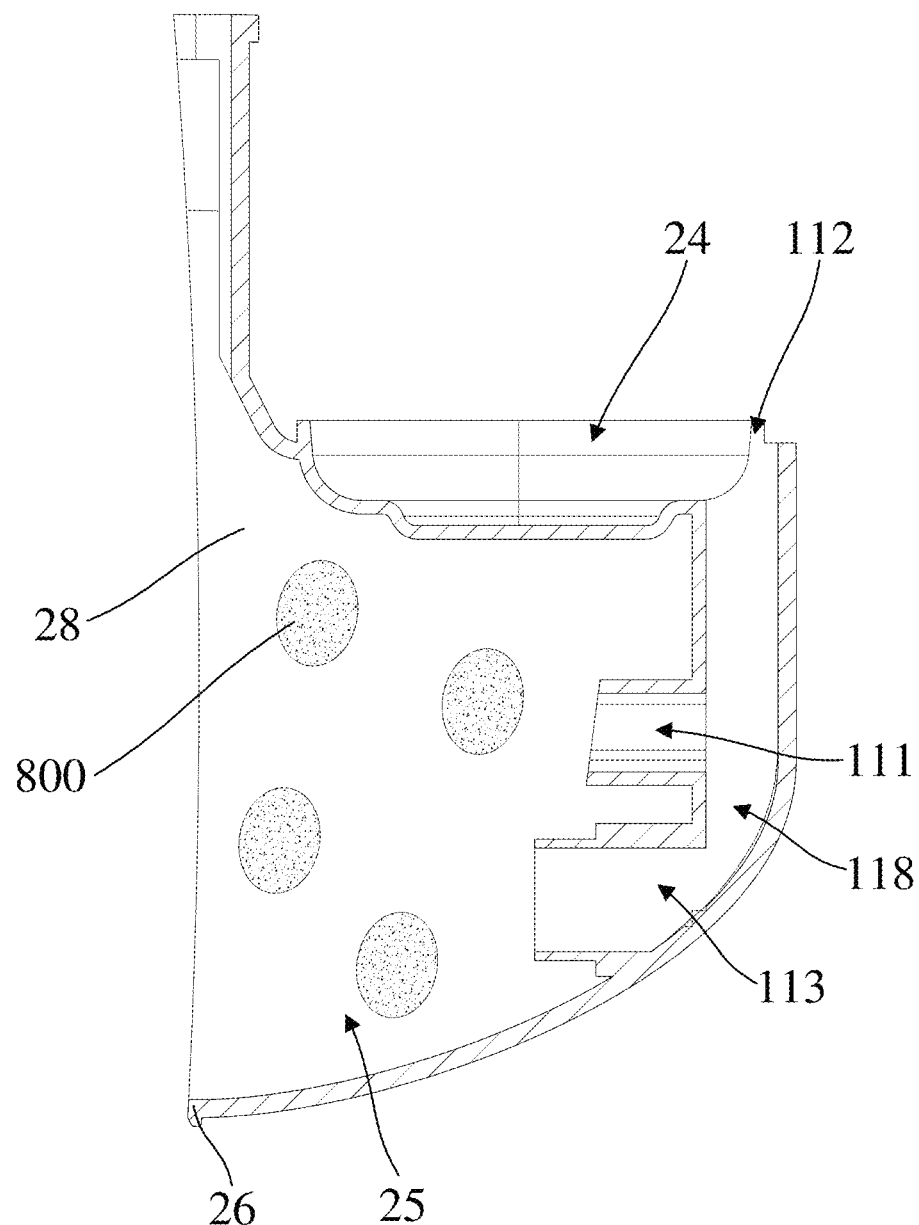
FIG. 4 is a schematic diagram illustrating a structure of a milk bowl of the wearable breast pump of FIG. 1.

Referring to FIG. 3 and FIG. 4, in some embodiments, the airbag 300 may be provided with an annular fixture hook 33. The annular fixture hook 33 is arranged along an edge 34 of the airbag 300. The bowl body 11 is provided with an annular fixture groove 119, and the annular fixture hook 33 is snap-fitted into the annular fixture groove 119 and covers at least a part of the negative pressure port 112.

Through the provision of the annular fixture hook 33 and the annular fixture groove 119, it is helpful to increase the contact area between the airbag 300 and the bowl body 11 and improve the connection stability of the airbag 300 with the bowl body 11, thereby reducing loosening of the airbag 30 from the bowl body 11; in addition, it is helpful to improve the sealing of the airbag 300 to the negative pressure port 112, thereby reducing the situation that the negative pressure in the channel 118 is insufficient due to leakage of the negative pressure port 112.

Figure 5:
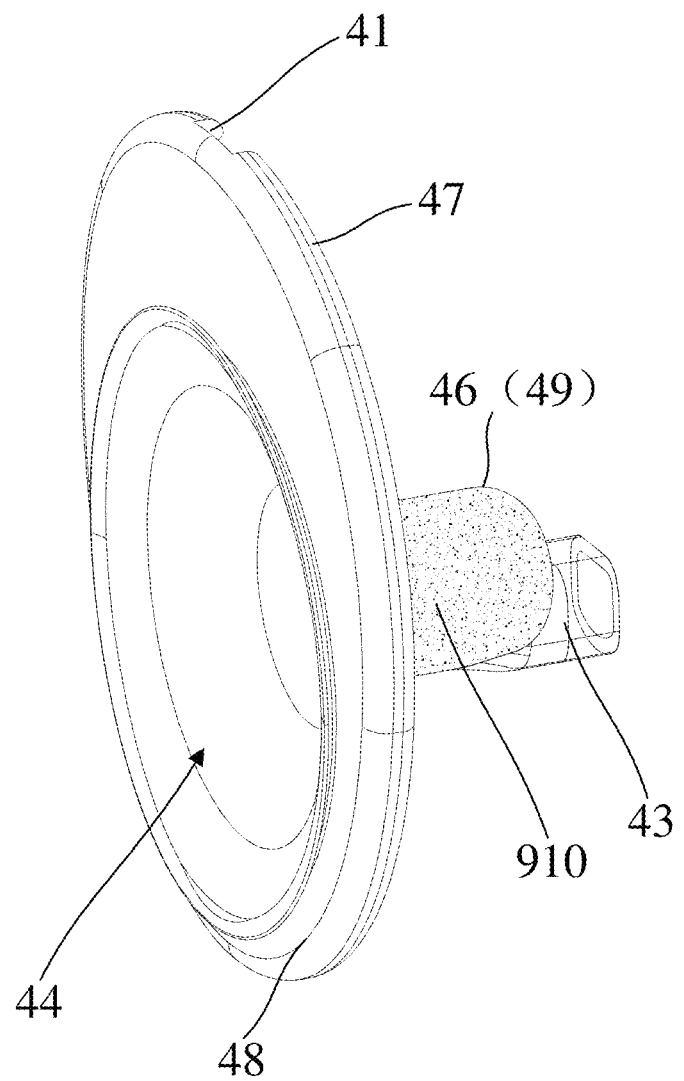
FIG. 5 is a schematic diagram illustrating a structure of a breast pump flange of the wearable breast pump of FIG. 1.
Figure 6:
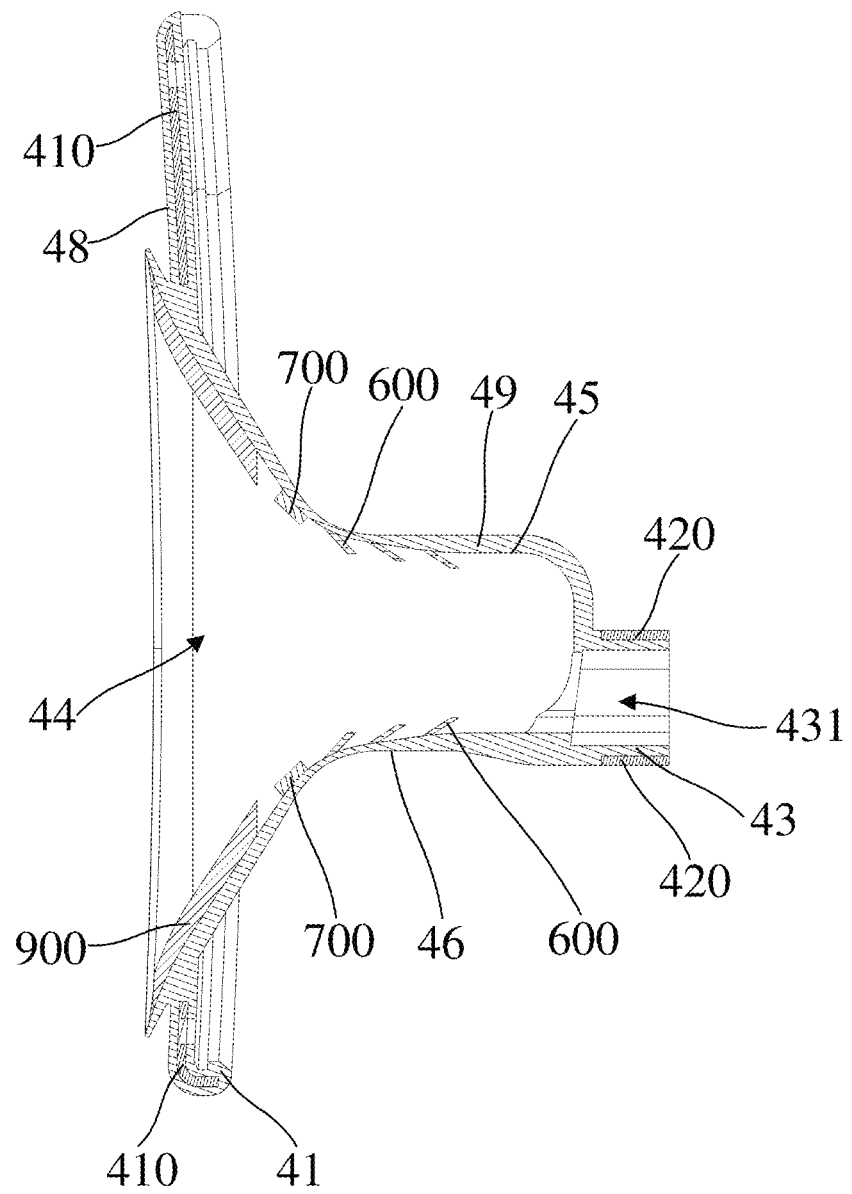
FIG. 6 is a longitudinal sectional view of the breast pump flange of FIG. 5.

Referring to FIG. 5 and FIG. 6, in some embodiments, the breast pump flange 400 may include an attachment frame 48, a main body 49 and a positioning pin 43. The attachment frame 48 is connected with the bowl body 11, and the positioning pin 43 is inserted into the milk sucking port 111. The milk sucking port 111 is communicated with the breast pump flange 400. For example, the positioning pin 43 may be provided with a connecting channel 431. The connecting channel 431 is communicated with the milk sucking port 111, and the breast milk in the breast pump flange 400 may flow through the connecting channel 431 to the milk sucking port 111.

Through the provision of the positioning pin 43, it is helpful to locate the connection position of the breast pump flange 400 with the bowl body 11, improve the connection accuracy of the breast pump flange 400 and the bowl body 11, and improve the assembly efficiency of the breast pump flange 400 with the bowl body 11. In addition, it is helpful to improve the connection stability of the breast pump flange 400 with the bowl body 11, and thus reduce disconnection of the breast pump flange 400 with the bowl body 11.

In some embodiments, the attachment frame 48, the main body 49 and the positioning pin 43 are integrally formed. For example, the attachment frame 48, the main body 49 and the positioning pin 43 may be formed into one piece through an integral molding process. In this way, it is helpful to reduce the number of the members of the breast pump flange 400 and facilitate the manufacture of the breast pump flange 400. In addition, it is helpful to reduce the number of molds of the members, and thus reduce the mold cost of the breast pump flange 400 Furthermore, it is also helpful to improve the sanitary condition and use convenience of the breast pump flange 400.

In some embodiments, the breast pump flange 400 may be a deformable breast pump flange. For example, the breast pump flange 400 can be a silicone breast pump flange which is deformable to better fit the user's breast shape, thereby improving the user's comfort when using the wearable breast pump 1000.

In some embodiments, the breast pump flange 400 may also include an air cushion 900. The air cushion 900 is attached onto an inner wall 45 of the main body 49, and located on a side of the breast pump flange 400 away from the milk sucking port 111. In this way, the air cushion 900 is deformable to adapt to different users' breast shapes, so that the air cushion 900 can fit to the user's breast, which helps to provide a comfortable sucking experience for the user.

The breast pump flange 400 may be provided with a support structure to support the breast pump flange 400, so that the breast pump flange 400 may maintain a certain shape while deforming, thereby better adapting to the user's breast shape.

In some embodiments, the breast pump flange 400 includes a first support member 410 and a second support member 420. The first support member 410 is annular and arranged at the attachment frame 48, and the second support member 420 is annular and arranged at the positioning pin 43. The first support member 410 and the second support member 420 each may be an annular plastic member and flat, which may be specifically set according to the actual situations.

In this way, the first support member 410 may support the attachment frame 48, so that the attachment frame 48 may maintain a certain shape while deforming, thereby better fitting to the bowl body 11 and the user's breast. The second support member 420 may support the positioning pin 43, so that the positioning pin 43 may maintain a certain shape while deforming, thereby facilitating better insertion and snap-fitting into the milk sucking port 111.

Referring to FIG. 2, FIG. 4, and FIG. 6, in some embodiments, the attachment frame 48 may be provided with a sealing portion 41. The sealing portion 41 is arranged along the circumferential edge 47 of the attachment frame 48. The bowl body 11 is provided with a milk storage cavity 25 and a sealing fit portion 26. The sealing portion 41 is connected with the sealing fit portion 26 to seal the milk storage cavity 25.

In this way, it facilitates to improve the sealing between the bowl body 11 and the attachment frame 48, reduce overflow of the breast milk from the milk storage cavity 25, and also reduce the contamination of an appearance surface of the bowl body 11 caused by the breast milk adhered to the appearance surface.

Exemplarily, the breast pump flange 400 may be trumpet-shaped, and the breast pump flange 400 may be provided with a breast accommodation cavity 44. The attachment frame 48 is located near the opening of the breast accommodation cavity 44, and the breast accommodation cavity 44 is communicated with the milk sucking port 111. The sealing portion 41 may be located on a side of the attachment frame 48 away from the breast accommodation cavity 44, and located at an edge position of the attachment frame 48. The sealing portion 41 may be a rolled edge flange. The sealing portion 41 may extend inward from the edge position of the attachment frame 48. The sealing fit portion 26 may be a rolled edge slot. The sealing fit portion 26 extends inward from the edge position of the bowl body 11. In this way, the sealing portion 41 and the sealing fit portion 26 help to improve the sealing between the bowl body 11 and the attachment frame 48, which helps to reduce leakage of the breast milk from the bowl body 11.

In some embodiments, the milk bowl 200 may also include a one-way valve 100. The one-way valve 100 is assembled to the bowl body 11 and located at the milk outlet 113. The one-way valve 100 may be a one-way duckbill valve.

In this way, the one-way valve 100 may be opened and communicated with the milk outlet 113 under the pressure of the breast milk, which ensures the normal milk discharge of the bowl body 11. In addition, it allows the breast milk to flow along a predetermined direction to the milk outlet 113, which facilitates reduction of backflow of the breast milk to the channel 118, and also facilitates reduction of overflow of the breast milk from the breast accommodation cavity 44.

Figure 7:
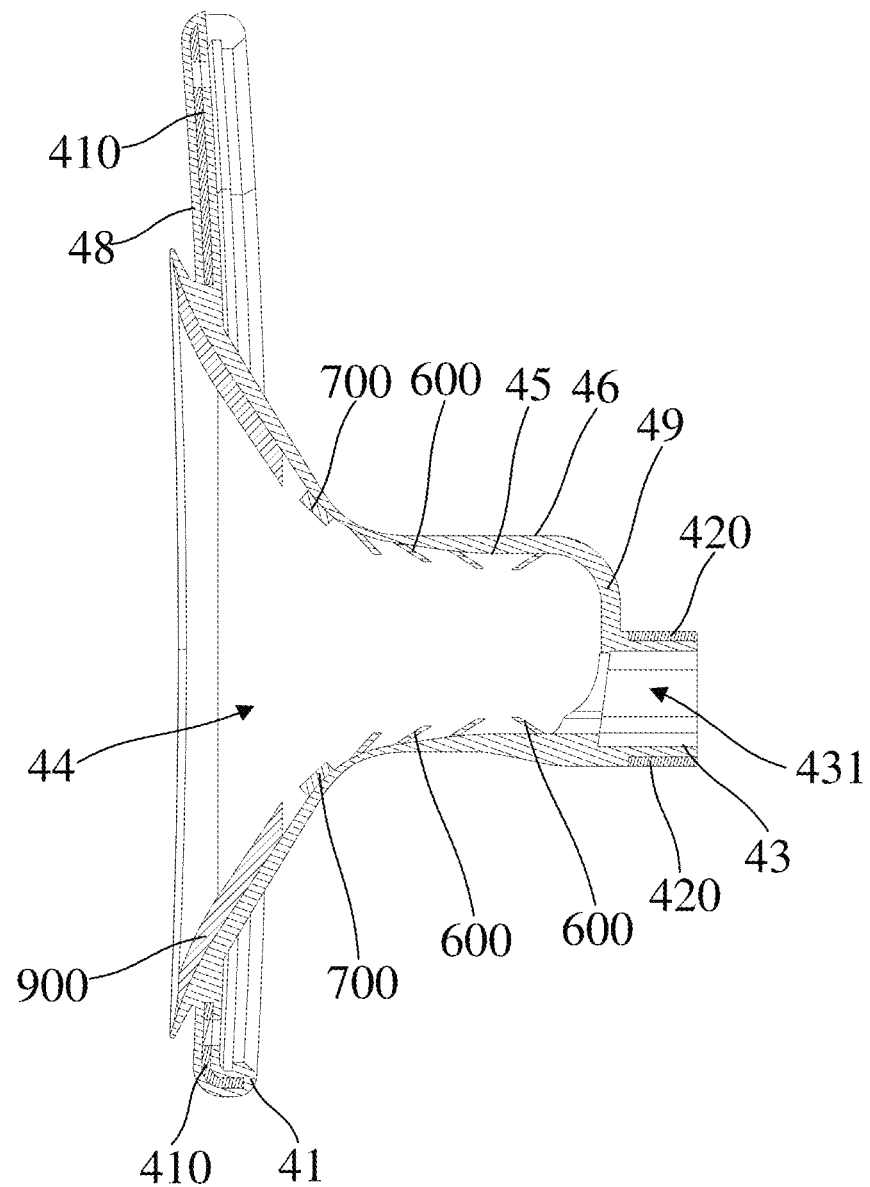
FIG. 7 is a longitudinal sectional view of another breast pump flange provided by the embodiments of the present disclosure.

Referring to FIG. 5 to FIG. 7, in some embodiments, the milk bowl 200 may also include multiple anti-overflow plates 600. The multiple anti-overflow plates 600 are arranged on the inner wall 45 of the main body 49, and spaced apart along the axial direction of the main body 49.

In this way, the multiple anti-overflow plates 600 can reduce the backflow of the breast milk from the milk sucking port 111 to the breast pump flange 400, and thus facilitates reduction of overflow of the breast milk from the breast accommodation cavity 44, thereby reducing waste of the breast milk. In the case of the multiple anti-overflow plates 600, if a part of the anti-overflow plates 600 near the milk sucking port are insufficient to block the breast milk, other anti-overflow plates 600 away from the milk sucking port 111 may further block the breast milk, so as to better reduce the overflow of the breast milk from the breast accommodation cavity 44.

In some embodiments, as shown in FIG. 6, the part of the anti-overflow plates 600 located away from the milk sucking port 111 are tilted in a direction facing toward the milk sucking port 111, or each anti-overflow plate 600 is tilted in the direction facing toward the milk sucking port 111. In this way, by tilting the anti-overflow plates 600 in the direction facing toward the emulsion suction port 111, it is helpful to guide the breast milk in the main body 49, so that the breast milk in the main body 49 can flow to the milk sucking port 111 along the predetermined direction.

In some embodiments, as shown in FIG. 7, the anti-overflow plates 600 near the milk sucking port 111 are inclined in a direction away from the milk sucking port 111. In this way, the main body 49 may have, at a position close to the milk sucking port 111, a large space to accommodate the breast milk, which is helpful to improve the anti-overflow effect of the anti-overflow plates 600.

In some embodiments, the milk bowl 200 further includes a vibrating massager 700, and the vibrating massager 700 is assembled inside the main body 49 and located near the anti-overflow plates 600. For example, the vibrating massager 700 is arranged on the inner wall 45 of the main body 49, and spaced from the multiple anti-overflow plates 600. In this way, the vibrating massager 700 may give, through vibration, a massage on the breast to imitate the sucking action of the baby, which is helpful to stimulate the breast to promote secretion of the breast milk, and thus reduces blockage of the breast. In addition, the vibration massager 700 may transmit the vibration to the anti-overflow plates 600, this enables the anti-overflow plates 600 protruding from the inner wall 45 of the cover 49 to transmit the vibration to the skin surface of the breast, so as to better stimulate the breast and thus promote the secretion of the breast milk.

In some embodiments, the milk bowl 200 may further include an annular heating film 910, and the annular heating film 910 is attached onto the main body 49 and extends along the axial direction of the main body 49.

In this way, the annular heating film 910 may heat the main body 49, so that the main body 49 may be maintained at an appropriate temperature. This helps to improve the comfort of the breast when the user wears the wearable breast pump 1000. It also helps to ensure that the breast milk flowing through the main body 49 can be maintained at an appropriate temperature, which reduces nutrient loss of the breast milk, and also improves the flow speed of the breast milk.

In some embodiments, the annular heating film 910 is located on an outer circumferential surface 46 of the main body 49. In this way, it may reduce burn injuries to the user that would be caused due to the direct contact between the annular heating film 910 and the user's breast. It is also helpful to reduce the thermal impact of the annular heating film 910 on the vibrating massager 700. The annular heating film 910 may be located on a different side of the main body 49 from the anti-overflow plates 600 and the vibration massager 700, and the outer circumferential surface 46 of the main body 49 may have large area to arrange the annular heating film 910.

Referring back to FIG. 2 and FIG. 4, in some embodiments, the wearable breast pump 1000 may further includes an electric heating element 800, and the electric heating element 800 is attached onto the inner wall 28 of the bowl body 11 and located in the milk storage cavity 25. The electric heating element 800 may be an electric heating film.

In this way, the electric heating element 800 may heat the inner wall 28 of the bowl body 11 and the breast milk in the milk storage cavity 25, so that the breast milk in the bowl body 11 and the milk storage cavity 25 can be maintained at a suitable temperature. It is helpful to reduce the nutrient loss of the breast milk, and facilitates direct feeding by the user or storage.

There may be multiple electric heating elements 800. For example, the number of the electric heating elements 800 may be two, three, four, or more. This helps to increase the heating area of the electric heating elements 800. Alternatively, the electric heating element 800 may cover the inner wall 28 of the bowl body 11, so that the whole of the inner wall 28 of the bowl body 11 is provided with the electric heating element 800. This can better improve the heating effect of the electric heating elements 800 on the inner wall 28 of the bowl body 11, and also ensure the consistency of the temperature of the inner wall 28 of the bowl body 11, which reduces the deterioration of the breast milk that would be caused by an excessive temperature difference of the breast milk in the milk storage cavity 25.

In some embodiments, the bowl body 11 is a transparent, and the outer surface of the bowl body 11 is provided with a capacity scale. In this way, the bowl body 11 can be integrated with functions of milk storage and metering. This helps the user to intuitively see the amount of the breast milk in the bowl body 11, and facilitates the user to selectively supplement breast milk to the bowl body 11 or discharge the breast milk from the bowl body 11 according to the amount of the breast milk.

In the embodiments of the present disclosure, unless otherwise specified or limited, the terms such as "assemble" should be interpreted broadly. For example, it may be a fixed connection, a detachable connection, or an integrated connection; or it may be a mechanical connection; or it may be a direct connection, an indirect connection through an intermediate medium, or an internal connection between two components; or it may merely be a surface contact connection, or a surface contact connection through an intermediate medium. For those ordinary skilled in the art, the specific meaning of the above terms in the present disclosure may be understood on a case-by-case basis.

In addition, the terms "first", "second", and etc. are only used to distinguish the description and cannot be understood as specific or special structures. The description of the term "some embodiments" means that the specific features, structures, materials, or characteristics described in conjunction with the embodiments or examples are included in at least one embodiment or example of the present disclosure. In the embodiments of the present disclosure, the schematic expressions of the above terms do not necessarily refer to the same embodiments or examples. Moreover, the specific features, structures, materials, or characteristics described can be combined in any one or more embodiments or examples in an appropriate manner. In addition, those skilled in the art can combine and associate different embodiments or examples described in the embodiments of the present disclosure, as well as the features of different embodiments or examples, without conflicting with each other.

The above embodiments are only used to illustrate the technical solutions of the embodiments of the present disclosure, and not to limit them. Although the embodiments of the present disclosure have been described in detail with reference to the aforementioned embodiments, those skilled in the art should understand that they can still modify the technical solutions described in the aforementioned embodiments, or equivalently replace some of the technical features. These modifications or substitutions do not depart from the essence and scope of the technical solutions of the respective embodiments of the present disclosure, and should be included within the scope of protection of the embodiments of the present disclosure.

What is claimed is:

1. A milk bowl for a wearable breast pump, the milk bowl comprising:
   a bowl body, wherein the bowl body is provided with a channel, a milk sucking port, a negative pressure port, a milk outlet and an airbag mounting groove, the milk sucking port, the negative pressure port and the milk outlet are spaced apart and are all communicated with the channel, and the negative pressure port is further communicated with the airbag mounting groove, wherein the bowl body is further provided with a milk storage cavity and a sealing fit portion;
   an airbag mounted in the airbag mounting groove, wherein a bottom of the airbag is in a wave shape when the airbag is in a natural state;
   a breast pump flange, comprising an attachment frame, a main body, a positioning pin, a first support member, and a second support member, wherein the attachment frame is connected with the bowl body, the attachment frame is provided with a sealing portion along a circumferential edge thereof, the sealing portion is a rolled edge flange, the sealing portion is connected with the sealing fit portion to seal the milk storage cavity, wherein the positioning pin is provided with a connecting channel, the connecting channel is communicated with the milk sucking port, wherein the first support member is annular, the first support member is embedded in the attachment frame, and a portion of the first support member is bent and embedded in the sealing portion, wherein the second support member is annular and arranged at the positioning pin; and
   a plurality of anti-overflow plates, wherein the anti-overflow plates are arranged spaced apart on an inner wall of the main body.

2. The milk bowl as claimed in claim 1, wherein the airbag is provided with an annular fixture hook, and the annular fixture hook is arranged along an edge of the airbag;
   the bowl body is further provided with an annular fixture groove, and the annular fixture hook is snap-fitted into the annular fixture groove and covers the negative pressure port.

3. The milk bowl as claimed in claim 1, wherein the milk bowl further comprises a vibrating massager, wherein the vibrating massager is assembled inside the main body and is located near the anti-overflow plates.

4. The milk bowl as claimed in claim 1, wherein the milk bowl further comprises an annular heating film, the annular heating film is attached onto the main body and extends along an axial direction of the main body, and the annular heating film is located on an outer circumferential surface of the main body.

5. The milk bowl as claimed in claim 1, wherein the milk bowl further comprises an electric heating element, and the electric heating element is attached onto an inner wall of the bowl body and located in the milk storage cavity.

6. The milk bowl as claimed in claim 1, wherein each anti-overflow plate is tilted in a direction towards the milk sucking port.

7. A wearable breast pump, comprising:
a main unit; and
a milk bowl, wherein the main unit is assembled to the milk bowl, the milk bowl comprises a bowl body, an airbag, a breast pump flange, and a plurality of anti-overflow plates; the bowl body is provided with a channel, a milk sucking port, a negative pressure port, a milk outlet and an airbag mounting groove; the milk sucking port, the negative pressure port and the milk outlet are spaced apart and are all communicated with the channel; the milk sucking port is further communicated with the breast pump flange; the airbag mounting groove is further communicated with the negative pressure port; the airbag is assembled in the airbag mounting groove; a bottom of the airbag is in a wave shape when the airbag is in a natural state;
wherein the bowl body is further provided with a milk storage cavity and a sealing fit portion;
wherein the breast pump flange comprises an attachment frame, a main body, a positioning pin, a first support member, and a second support member; the attachment frame is connected with the bowl body, the attachment frame is provided with a sealing portion along a circumferential edge thereof, the sealing portion is a rolled edge flange, the sealing portion is connected with the sealing fit portion to seal the milk storage cavity; wherein the positioning pin is provided with a connecting channel, the connecting channel is communicated with the milk sucking port; wherein the first support member is annular, the first support member is embedded in the attachment frame, and a portion of the first support member is bent and embedded in the sealing portion; wherein the second support member is annular and arranged at the positioning pin;
wherein the anti-overflow plates are arranged on an inner wall of the main body, and are spaced apart along an axial direction of the main body.

8. The wearable breast pump as claimed in claim 7, wherein the airbag is provided with an annular fixture hook, and the annular fixture hook is arranged along an edge of the airbag; the bowl body is further provided with an annular fixture groove, and the annular fixture hook is snap-fitted into the annular fixture groove and covers the negative pressure port.

9. The wearable breast pump as claimed in claim 7, wherein the attachment frame, the main body and the positioning pin are integrally formed.

10. The wearable breast pump as claimed in claim 7, wherein the milk bowl further comprises an annular heating film, the annular heating film is attached onto the main body and extends along an axial direction of the main body, and the annular heating film is located on an outer circumferential surface of the main body.

11. The wearable breast pump as claimed in claim 7, wherein the milk bowl further comprises an electric heating element, and the electric heating element is attached onto an inner wall of the bowl body and located in the milk storage cavity.

12. The wearable breast pump as claimed in claim 7, wherein the bowl body is transparent.

13. The wearable breast pump as claimed in claim 7, wherein the main unit comprises a power supply, a controller and a vacuum pump, the controller is electrically connected with the power supply, the controller is configured to communicate with the vacuum pump though signal, and the vacuum pump is connected with the airbag.

14. The wearable breast pump as claimed in claim 7, wherein each anti-overflow plate is tilted in a direction towards the milk sucking port.

15. The wearable breast pump as claimed in claim 7, wherein some anti-overflow plates near the milk sucking port are inclined towards a direction away from the milk sucking port.

16. The wearable breast pump as claimed in claim 7, wherein the milk bowl further comprises a vibrating massager, the vibrating massager is arranged on the inner wall of the main body and spaced from the anti-overflow plates, and the vibrating massager is configured to transmit a vibration to the anti-overflow plates.

17. The wearable breast pump as claimed in claim 7, wherein some anti-overflow plates near the milk sucking port are inclined towards a direction away from the milk sucking port, and the others are tilted in a direction towards the milk sucking port.

* * * * *